(12) United States Patent
Janka et al.

(10) Patent No.: US 9,029,579 B2
(45) Date of Patent: *May 12, 2015

(54) METHOD OF SYNTHESIZING LOW COLOR FURAN DIESTERS

(71) Applicant: Eastman Chemical Company, Kingsport, TN (US)

(72) Inventors: Mesfin Ejerssa Janka, Kingsport, TN (US); John Dayton Baker, Jr., Kingsport, TN (US); Stephanie Nicole Rollins, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/672,022

(22) Filed: Nov. 8, 2012

(65) Prior Publication Data

US 2014/0128624 A1 May 8, 2014

(51) Int. Cl.
| | | |
|---|---|---|
| C07D 307/62 | (2006.01) | |
| C07D 307/68 | (2006.01) | |
| C07D 307/18 | (2006.01) | |
| C07D 307/24 | (2006.01) | |

(52) U.S. Cl.
CPC ............ C07D 307/68 (2013.01); C07D 307/18 (2013.01); C07D 307/24 (2013.01)

(58) Field of Classification Search
USPC .......................................... 549/485; 208/264
See application file for complete search history.

(56) References Cited

U.S. PATENT DOCUMENTS

| | | | | |
|---|---|---|---|---|
| 2,819,289 | A * | 1/1958 | Luben ............................. | 208/27 |
| 3,225,066 | A | 12/1965 | Lew | |
| 3,259,636 | A | 7/1966 | Lew | |
| 3,546,255 | A | 12/1970 | Duennenberger et al. | |
| 3,994,931 | A * | 11/1976 | Johnson et al. ............... | 549/505 |
| 7,385,081 | B1 * | 6/2008 | Gong ............................. | 562/405 |
| 8,796,477 | B2 * | 8/2014 | Janka et al. .................... | 549/485 |
| 2011/0263916 | A1 * | 10/2011 | Bao et al. ...................... | 585/254 |

FOREIGN PATENT DOCUMENTS

| | | |
|---|---|---|
| EP | 2 481 773 A1 | 8/2012 |
| GB | 819438 A | 9/1959 |
| WO | WO 2011/023491 A1 | 3/2011 |
| WO | WO 2012-017052 A1 | 2/2012 |
| WO | WO 2012/002681 A1 | 3/2012 |
| WO | WO 2012/161970 A2 | 11/2012 |

OTHER PUBLICATIONS

Sanderson, R. D., et al.; Synthesis and Evaluation of Dialkyl Furan-2,5-Dicarboxylates as Plasticizers for PVC, Journal of Applied Polymer Science, vol. 53, (1994), pp. 1785-1793.
Copending U.S. Appl. No. 13/671,941, filed on Nov. 8, 2012, Mesfin Ejerssa Janka.
Notification of Transmittal of the International Search Report and the Written Opinion of the International Searching Authority, or the Declaration; International Application No. PCT/US2013/068423; Mailing Date: Apr. 7, 2014.
USPTO Office Action dated Oct. 3, 2013 in co-pending U.S. Appl. No. 13/671,941.
Notification of Transmittal of the International Search Report and the Written Opinion of the International Searching Authority, or the Declaration; International Application No. PCT/US2013/068419; Mailing Date: Dec. 12, 2013.
Lewkowski, J; Convenient Synthesis of Furan-2,5-dicarboxylic Acid and Its Derivatives; Polish Journal of Chemistry, vol. 75, pp. 1943-1946 (2001).
USPTO Office Action dated Aug. 29, 2014 in co-pending U.S. Appl. No. 13/671,941.
USPTO Notice of Allowance dated Feb. 10, 2015 in co-pending U.S. Appl. No. 13/671,941.

* cited by examiner

*Primary Examiner* — Noble Jarrell
*Assistant Examiner* — Raymond Covington
(74) *Attorney, Agent, or Firm* — Denis V. Carmen

(57) ABSTRACT

The present invention relates to a method of making low colored bis(2-ethylhexyl) furan-2,5-dicarboxylate (BEHFD) plasticizer via mild hydrogenation of highly colored BEHFD.

26 Claims, No Drawings

METHOD OF SYNTHESIZING LOW COLOR FURAN DIESTERS

BACKGROUND

Plasticizers have the ability to reduce the glass transition temperature of polymers and thereby provide soft and/or flexible products. Plasticizers are often based on esters of polycarboxylic acids with linear or branched aliphatic alcohols of moderate chain length. Organic ester phthalates are widely used plasticizers. The most commonly used phthalate esters are di-2-ethylhexyl phthalate (DEHP), also known as dioctyl phthalate (DOP), diisononyl phthalate (DINP) and diisodecyl phthalate (DIDP). These aromatic dicarboxylic plasticizers are commonly synthesized from terephthalic acid or dimethyl terephthalate and the corresponding alcohol. There is a growing interest in the use of renewable resources as feed stocks for the chemical industries mainly due to the progressive reduction of fossil reserves and their related environmental impacts.

Furan-2,5-dicarboxylic acid (FDCA) is a versatile intermediate considered as a promising closest biobased alternative to terephthalic acid. Like aromatic diacids, FDCA undergoes esterification reaction with an alcohol such as 2-ethylhexanol to form bis(2-ethylhexyl) furan-2,5-dicarboxylate (BEHFD) plasticizer. BEHFD plasticizers can be synthesized from FDCA and 2-ethylhexan-1-ol (2-EH), in the presence of a catalyst as shown below in equation (1), or by transesterification of dimethyl furan-2,5-dicarboxylate (DMFD) with 2-EH in the presence of a catalyst as shown below in equation (2).

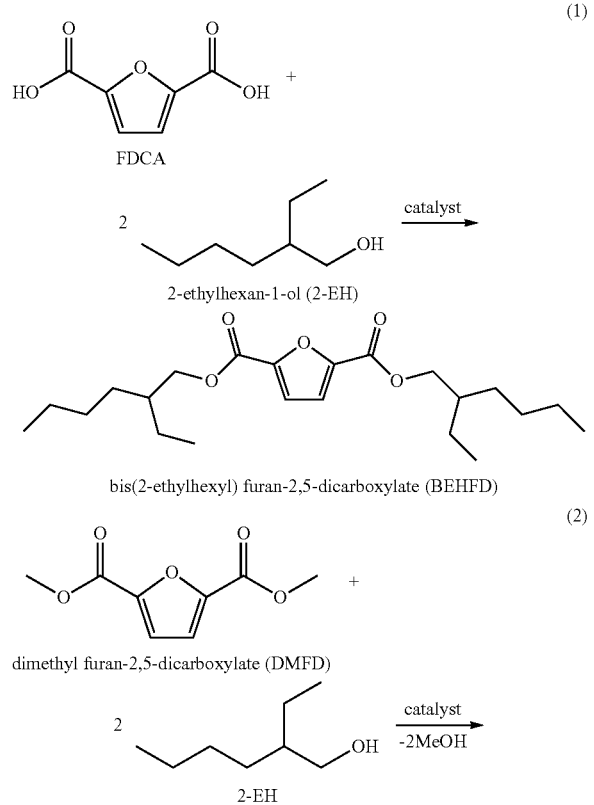

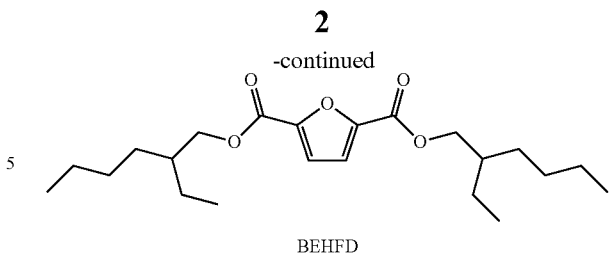

BEHFD

However, the above synthetic pathways to make BEHFD yield very highly colored plasticizer which makes its end use application less desirable.

SUMMARY

This summary is provided to introduce simplified concepts of producing low color furan based diesters. Additional details of example methods are further described below in the Detailed Description. This summary is not intended to identify essential features of the claimed subject matter, nor is it intended for use alone in determining the scope of the claimed subject matter.

According to an embodiment, the present invention concerns a method for preparing a low color furan-2,5-dicarboxylate derivative plasticizer, comprising:
 a) providing a furan-2,5-dicarboxylate derivative; and
 b) contacting the furan-2,5-dicarboxylate derivative with hydrogen in the presence of a hydrogenation catalyst to thereby produce a low color furan-2,5-dicarboxylate derivative plasticizer having an APHA of less than 100.

Another embodiment concerns a method for producing a low color furan-2,5-dicarboxylate derivative, comprising:
 a) contacting a furan-2,5-dicarboxylic acid composition and an alcohol stream in the presence of an esterification catalyst under esterification conditions to produce a furan-2,5-dicarboxylate derivative;
 b) contacting the furan-2,5-dicarboxylate derivative with hydrogen in the presence of a hydrogenation catalyst to thereby produce a low color furan-2,5-dicarboxylate derivative plasticizer having an APHA of less than 100.

DETAILED DESCRIPTION

According to an embodiment, the present invention concerns a method to make low colored furan-2,5-dicarboxylate derivative plasticizers, such as BEHFD, by the hydrogenation of colored BEHFD.

It should be understood that the following is not intended to be an exclusive list of defined terms. Other definitions may be provided in the foregoing description, such as, for example, when accompanying the use of a defined term in context.

As used herein, the terms "a," "an," and "the" mean one or more.

As used herein, the terms "comprising," "comprises," and "comprise" are open-ended transition terms used to transition from a subject recited before the term to one or more elements recited after the term, where the element or elements listed after the transition term are not necessarily the only elements that make up the subject.

As used herein, the terms "having," "has," "contain," "including," "includes," "include," and "have" have the same open-ended meaning as "comprising," "comprises," and "comprise" provided above.

The present description uses numerical ranges to quantify certain parameters relating to the invention. It should be understood that when numerical ranges are provided, such ranges are to be construed as providing literal support for claim limitations that only recite the lower value of the range as well as claim limitations that only recite the upper value of the range. For example, a disclosed numerical range of 10 to 100 provides literal support for a claim reciting "greater than 10" (with no upper bounds) and a claim reciting "less than 100" (with no lower bounds) and provided literal support for and includes the end points of 10 and 100.

The present description uses specific numerical values to quantify certain parameters relating to the invention, where the specific numerical values are not expressly part of a numerical range. It should be understood that each specific numerical value provided herein is to be construed as providing literal support for a broad, intermediate, and narrow range. The broad range associated with each specific numerical value is the numerical value plus and minus 60 percent of the numerical value, rounded to two significant digits. The intermediate range associated with each specific numerical value is the numerical value plus and minus 30 percent of the numerical value, rounded to two significant digits. The narrow range associated with each specific numerical value is the numerical value plus and minus 15 percent of the numerical value, rounded to two significant digits. These broad, intermediate, and narrow numerical ranges should be applied not only to the specific values, but should also be applied to differences between these specific values.

All amounts are by weight unless otherwise specified. All amounts by weight are based on the weight of the whole composition stream containing the ingredient in question rather than a part of that composition or a different stream altogether, unless otherwise noted. All stated amounts in ppm are by weight (ppmw) unless otherwise noted.

According to an embodiment, the present disclosure concerns a method of producing a low colored furan-2,5-dicarboxylate derivative plasticizer via the hydrogenation of a furan-2,5-dicarboxylate derivative composition. Moreover, the low colored furan-2,5-dicarboxylate derivative plasticizers obtained by the methods described herein show good fusion, lower volatility and better efficiency than DEHP for PVC application. As used herein, "low colored furan-2,5-dicarboxylate derivative" means a furan-2,5-dicarboxylate derivative having an APHA color of less than 100; less than 60 less than 40; or less than 20. Alternatively, "low colored furan-2,5-dicarboxylate derivative" means a furan-2,5-dicarboxylate derivative having a b* value of less than 10; less than 5.0 less than 2.0; or less than 1.0.

According an embodiment, the present description concerns a method for producing a low color furan-2,5-dicarboxylate derivative, such as BEHFD, which includes contacting a furan-2,5-dicarboxylic acid composition and an alcohol stream in the presence of a catalyst under esterification conditions to produce a furan-2,5-dicarboxylate derivative composition, and hydrogenating the furan-2,5-dicarboxylate derivative composition. Moreover, the post hydrogenation furan-2,5-dicarboxylate derivative composition has an APHA color of less than 100; less than 60 less than 40; or less than 20 and/or a b* value of less than 10; less than 5.0 less than 2.0; or less than 1.0.

Alcohols useful in the alcohol stream can include, but are not limited to, iso-, normal, branched, unbranched, linear, cyclo and/or aryl isomers of $C_4$ to $C_{13}$ alcohols or mixtures thereof. Examples of such alcohols include butanol, pentanol, hexanol, heptanol, octanol (including 2-ethylhexanol), nonanol, decanol, undecanol, dodecanol, 2-phenyl ethanol, cyclohexanol, cyclohexanemethanol, methylcyclo-hexanemethanol, 1,4-cyclohexanedimethanol, benzyl alcohol and mixtures thereof. According to an embodiment, the alcohol stream can include a mixture of two or more alcohols.

Moreover, examples of the type of furan-2,5-dicarboxylate derivatives that can be produced include, but are not limited to dibutyl furan-2,5-dicarboxylate, dipentyl furan-2,5-dicarboxylate, dihexyl furan-2,5-dicarboxylate, diheptyl furan-2,5-dicarboxylate, bis(2-ethylhexyl) furan-2,5-dicarboxylate, bis(dioctyl) furan-2,5-dicarboxylate, bis(dibenzyl) furan-2,5-dicarboxylate, bis(dinonyl) furan-2,5-dicarboxylate, and bis(didecyl) furan-2,5-dicarboxylate, mixed alcohol derivatives, and mixtures of furan dicarboxylic acid esters and other plasticizers in varying ratios.

In an embodiment, the esterification process useful for producing a furan-2,5-dicarboxylate derivative prior to hydrogenation can be carried out in a reaction zone comprising a pressure vessel while maintaining the alcohol:furan diester mole ratio of from about 10:1.0 to about 0.8:1.0; from about 5.0:1.0 to about 1.0:1.0; or from about 3.0:1.0 to about 2.0:1.

The pressure within the reaction zone can be maintained from about 150 psig to about 15 psig (atmospheric pressure); from about 75 psig to about 15 psig; or from about 30 psig to about 15 psig. Alternatively, the pressure in the reaction zone can be maintained at below 150 psig, below 125 psig, below 100 psig, below 75 psig, below 50 psig, or below 25 psig. According to another embodiment, the pressure in the reaction zone can be maintained at above 10 psig, above 15 psig, above 25 psig, above 50 psig, above 75 psig, above 100 psig, or above 125 psig.

The temperature within the reaction zone can be maintained from about 300° C. to about 20° C. (room temperature); from about 250° C. to about 100° C.; or from about 200° C. to about 150° C. Alternatively, the temperature in the reaction zone can be maintained at below 300° C., below 250° C., below 200° C., below 150° C., below 125° C., below 100° C., below 75° C., below 50° C., below 40° C., or below 30° C. According to another embodiment, the temperature in the reaction zone can be maintained at above 20° C., above 50° C., above 75° C., above 100° C., above 125° C., above 150° C., above 175° C., above 200° C., above 250° C., or above 275° C.

The esterification catalyst may be a compound soluble in the esterification reaction mixture, i.e., soluble in the alcohol and the furan diester product. For example, the catalyst can be, but is not limited to, dibutyltin diacetate, dibutyltin oxide, titanium tetraisopropoxide, zirconium derivatives, iron derivatives, sulfuric acid, methanesulfonic acid, hydrochloric acid or mixtures thereof.

According to an embodiment, the hydrogenation of the furan-2,5-dicarboxylate derivative composition includes contacting a furan-2,5-dicarboxylate derivative composition with hydrogen under hydrogenation conditions in the presence of a catalyst and, alternatively, separating at least a portion of the furan-2,5-dicarboxylate derivative from the furan-2,5-dicarboxylate derivative composition to produce a low color furan-2,5-dicarboxylate derivative composition.

Any of the known hydrogenation reactor designs or configurations may be used in carrying out the hydrogenation process. For example, the process may be conducted in a batchwise manner in an autoclave by contacting the furan-2,5-dicarboxylate derivative composition with hydrogen in the presence of a hydrogenation catalyst.

The amount of catalyst required can be varied substantially depending on a number of factors such as, for example, the composition and physical form of the catalyst and the hydrogenation conditions and mode of operation being used. The hydrogenation conditions of pressure and temperature also can be varied depending not only on one another but also on the activity of the catalyst, the mode of operation, selectivity considerations and the desired rate of conversion. For example, the pressure within the reaction zone can be maintained from about 10 psig to about 1000 psig; from about 20 psig to about 900 psig; or from about 50 psig to about 500 psig. Alternatively, the pressure in the reaction zone can be maintained at below 1000 psig, below 900 psig, below 800 psig, below 700 psig, below 600 psig, below 500 psig, below 400 psig, below 300 psig, below 200 psig, below 100 psig, below 50 psig, or below 25 psig. According to another embodiment, the pressure in the reaction zone can be maintained at above 10 psig, above 25 psig, above 50 psig, above 100 psig, above 200 psig, above 300 psig, above 400 psig, above 600 psig, above 700 psig, above 800 psig or above 900 psig.

The hydrogenation temperature within the reaction zone can be maintained from about 50° C. to about 300° C.; from about 100° C. to about 250° C.; or from about 100° C. to about 200° C. Alternatively, the temperature in the reaction zone can be maintained at below 300° C., below 250° C., below 200° C., below 150° C., below 125° C., below 100° C., below 75° C., or below 60° C. According to another embodiment, the temperature in the reaction zone can be maintained at above 50° C., above 75° C., above 100° C., above 125° C., above 150° C., above 175° C., above 200° C., above 250° C., or above 275° C. While rates and conversions generally also increase with increasing pressure, the energy costs for compression of hydrogen, as well as the increased cost of high-pressure equipment render the use of the lowest pressure practical desirable.

The hydrogen gas used in the process may comprise fresh gas or a mixture of fresh gas and recycle gas. The hydrogen gas can be a mixture of hydrogen, optional minor amounts of components such as CO and $CO_2$, and inert gases, such as argon, nitrogen, or methane, containing at least about 70 mole % of hydrogen. For example, the hydrogen gas may contain at least 90 mole % or, in another example, at least 97 mole %, of hydrogen. The hydrogen gas may be obtained from any of the common sources well known in the art such as, for example, by partial oxidation or steam reforming of natural gas. Pressure swing absorption can be used if a high purity hydrogen gas is desired. If gas recycle is utilized in the process, then the recycle gas will normally contain minor amounts of one or more products of the hydrogenation reaction which have not been fully condensed in the product recovery stage downstream from the hydrogenation zone.

According to an embodiment, known hydrogenation catalysts may be used to hydrogenate the BEHFD. For example, suitable catalysts include, but are not limited to nickel, palladium, platinum, ruthenium, or rhenium in finely divided state or deposited on such catalyst supports as activated carbon, silica gel, or alumina.

EXAMPLES

The process according to the embodiments described above is further illustrated by, but not limited to, the following examples wherein all percentages given are by weight unless specified otherwise.

Analytical

BEHFD Color Measurement:

Samples were analyzed using a Hunter Lab UltraScan Pro spectrophotometer with a diffuse illumination integrating light sphere. Per manufacturer recommendation the spectrophotometer was set to the CIELAB color scale with the D65 illuminate and 10° observer. The BEHFD neat liquid sample was transferred to a clear, disposable transmission cell having a 20 mm path length. The spectrophotometer was standardized in total transmission mode with an empty disposable transmission cell. The purpose of this standardization was to subtract the background color response of the cell from the BEHFD sample. The transmission of each sample was then measured to obtain the CIELAB value for b* and APHA value using a Hunterlab EasyQuest QC software, version 4.30.

The Platinum-Cobalt Scale (Pt/Co Scale or Apha-Hazen Scale):

the Platinum-Cobalt Scale (Pt/Co Scale or Apha-Hazen Scale) is also used to visually determine color of the sample by comparison. Color analysis on the final material was conducted using the visual comparison color method and the standard APHA color scale samples.

BEHFD Synthesis Using Crude FDCA (BEHFD Synthesis A):

The following reaction was conducted twice and the results are shown below in Table 1 as Examples 1 and 2 respectively. Crude FDCA that contains 4000 ppm of FFCA was converted to BEHFD plasticizer via the following reaction. A 2000 mL round bottom flask was fitted with an agitator and inlet port to supply a nitrogen atmosphere. The outlet port had a Dean-Stark trap and condenser to capture water and 2-ethylhexanol alcohol as it was removed from the reactor. To the reactor was added 350 g commercial FDCA and 700 g 2-EH alcohol along with 140 mL toluene to aid the removal of water from the reaction. Also, the following was added: 21 mL Methanesulfonic acid and 10.5 mL 50% hypophosphorous acid as catalyst. The reaction mixture was heated to 125-128° C. pot temperature and the water removal monitored until it has stopped coming over or the theoretical amount was captured in the Dean-Stark trap. To the reaction mixture was added 5 mL 50% hypophosphorous acid and the mixture was heated for 15 minutes. The reaction mixture temperature was adjusted to 50° C. and 300 mL toluene added. 400 mL 4% NaOH water solution was added to wash the organic layer, which was allowed to settle, and then the aqueous bottom layer was separated. 400 mL 5% NaHCO3 water solution was added to wash the organic layer, which was allowed to settle, and then the aqueous bottom layer was separated. The organic layer was dried over MgSO4 rinsing with 20-50 mL toluene. The toluene and product were heated to strip the toluene using vacuum (120-125 mm) to a pot temperature of 120-125° C. Then continued heating to 130-135° C. and increased the vacuum (18-22 mm) to remove the 2-ethylhexanol. The reaction mixture was cooled to 20-25° C. and the APHA color measured to be 200 visually (APHA color is ~216 instrumentally). A weight yield of 69-82% BEHFD was obtained. GC analysis gave 93.7% BEHFD and 4.6% 2-Ethyhexanol as the major components.

Two samples of BEHFD Synthesis A were hydrogenated via the hydrogenation process shown below and the results are shown as Examples 1 and 2 in Table 1 below.

BEHFD Synthesis Using Crude FDCA (BEHFD Synthesis B):

Crude FDCA that contains 4000 ppm of FFCA was converted to BEHFD plasticizer via the following reaction. A 2000 mL round bottom flask was fitted with an agitator and inlet port to supply a nitrogen atmosphere. The outlet port had a Dean-Stark trap and condenser to capture water and 2-ethylhexanol alcohol as it was removed from the reactor. To the reactor was added 350 g commercial FDCA and 720 g 2-EH alcohol along with 3.96 g dibutyltin diacetate as catalyst. The reaction mixture was heated to 165° C. and the water removal monitored until it had stopped coming over or the theoretical amount was captured in the Dean-Stark trap. The reaction mixture was cooled to 75° C. and washed with the following. A 4% sodium hydroxide aqueous solution was added to the reaction mixture, agitated, settled and the bottom aqueous layer decanted. A 4% sodium bicarbonate aqueous solution was added to the reaction mixture, agitated, settled, and bottom aqueous layer decanted. The reaction mixture was dried over magnesium sulfate and filtered through a Celite pad. A weight of 857 g of BEHFD was obtained with a GC assay of 87.1% product and 11.96% 2-Ethylhexanol.

Analytical: GC Analysis—87.1% Di-(2-ethylhexyl)furandicarboxylate 11.96% 2-ethylhexanol Platinum-Cobalt Scale (Pt/Co scale or Apha-Hazen Scale): >500 APHA Color using the visual scale.

Instrumental APHA color was 393.68

One sample of BEHFD Synthesis B was hydrogenated via the hydrogenation process shown below and the results are shown as Example 3 in Table 1 below.

Hydrogenation of Colored BEHFD Procedure:

A 300 mL autoclave equipped with a catalyst basket was charged with 109.0 g of colored BEHFD liquid. The catalyst basket was charged with 12.5 g of a palladium/carbon catalyst containing 0.5 wt. % palladium (CBA-300 SE 11233). The autoclave was sealed and heated to 170° C. while agitating the mixture. Hydrogen gas was introduced to attain 300 psig total pressure. The total pressure was maintained from a surge tank of hydrogen gas during the reaction. The reaction continued for 3 hours and gas supply was stopped and the autoclave was cooled to room temperature and depressurized. The liquid product was filtered to remove catalyst particulates. Hydrogenation was conducted on two samples from BEHFD Synthesis A (Examples 1 and 2 from Table 1) and one sample of BEHFD Synthesis B (Example 3 from Table 1). Moreover, the three liquid products from each sample were analyzed by CIE color measurement method. Analytical results are given in Table 1.

TABLE 1

Results from the mild hydrogenation of colored BEHFD.

| | Before Hydrogenation | | After hydrogenation | |
|---|---|---|---|---|
| Example | b* | APHA | b* | APHA |
| 1 | 14.02 | 215.75 | 1.81 | 24.39 |
| 2 | 14.02 | 215.75 | 1.22 | 17.52 |
| 3 | 24.93 | 393.68 | 3.56 | 38.12 |

Interpretation of Results:

Mild Hydrogenation of Colored BEHFD:

Esterification of crude FDCA with 2-EH in presence of dibutyltin diacetate catalyst produced a highly colored BEHFD with APHA color of 200-400. Mild hydrogenation of the colored BEHFD using Pd on carbon catalyst produced BEHFD with APHA color of approximately 20-40, Table 1. These comparative examples demonstrate that mild hydrogenation is an efficient process to mitigate the color issue and hence make BEHFD more desirable.

The following components were identified in the low color BEHFD sample by GC/MS:

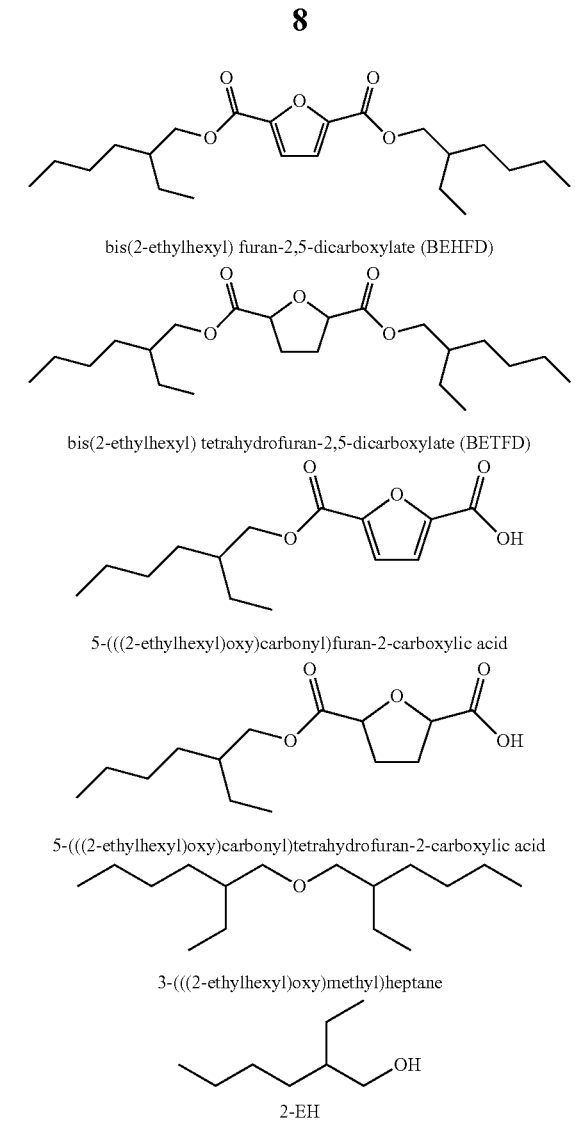

Although embodiments have been described in language specific to methodological acts, the embodiments are not necessarily limited to the specific acts described. Rather, the specific acts are disclosed as illustrative forms of implementing the embodiments.

What is claimed is:

1. A method for preparing a low color furan-2,5-dicarboxylate derivative plasticizer, comprising contacting a furan-2,5-dicarboxylate derivative with hydrogen in the presence of a hydrogenation catalyst to thereby produce a low color furan-2,5-dicarboxylate derivative plasticizer.

2. The method according to claim 1, wherein the furan-2,5-dicarboxylate derivative plasticizer has an APHA of less than 100.

3. The method according to claim 2, wherein the furan-2,5-dicarboxylate derivative plasticizer has an APHA of less than 60.

4. The method according to claim 3, wherein the furan-2,5-dicarboxylate derivative plasticizer has an APHA of less than 40.

5. The method according to claim 4, wherein the furan-2,5-dicarboxylate derivative plasticizer has an APHA of less than 20.

6. The method according to claim 1, wherein the furan-2,5-dicarboxylate derivative plasticizer has a b* value of less than 10.

7. The method according to claim 6, wherein the furan-2,5-dicarboxylate derivative plasticizer has a b* value of less than 5.

8. The method according to claim 1, wherein the furan-2,5-dicarboxylate derivative plasticizer comprises dibutyl furan-2,5-dicarboxylate, dipentyl furan-2,5-dicarboxylate, dihexyl furan-2,5-dicarboxylate, diheptyl furan-2,5-dicarboxylate, bis(2-ethylhexyl) furan-2,5-dicarboxylate, bis(dioctyl) furan-2,5-dicarboxylate, bis(dibenzyl) furan-2,5-dicarboxylate, bis(dinonyl) furan-2,5-dicarboxylate, bis(didecyl) furan-2,5-dicarboxylate or mixtures thereof.

9. The method according to claim 1, wherein the hydrogenation catalyst comprises a nickel catalyst, a palladium catalyst, a platinum catalyst, a ruthenium catalyst, or a rhenium catalyst or mixtures thereof.

10. A method for producing a low color furan-2,5-dicarboxylate derivative, comprising:
    a) contacting a furan-2,5-dicarboxylic acid composition and an alcohol stream in the presence of an esterification catalyst under esterification conditions to produce a furan-2,5-dicarboxylate derivative;
    b) contacting the furan-2,5-dicarboxylate derivative with hydrogen in the presence of a hydrogenation catalyst to thereby produce a low color furan-2,5-dicarboxylate derivative plasticizer.

11. The method according to claim 10, wherein the furan-2,5-dicarboxylate derivative plasticizer has an APHA of less than 100.

12. The method according to claim 11, wherein the furan-2,5-dicarboxylate derivative plasticizer has an APHA of less than 60.

13. The method according to claim 12, wherein the furan-2,5-dicarboxylate derivative plasticizer has an APHA of less than 40.

14. The method according to claim 13, wherein the furan-2,5-dicarboxylate derivative plasticizer has an APHA of less than 20.

15. The method according to claim 10, wherein the furan-2,5-dicarboxylate derivative plasticizer has a b* value of less than 10.

16. The method according to claim 15, wherein the furan-2,5-dicarboxylate derivative plasticizer has a b* value of less than 5.

17. The method according to claim 8, wherein the alcohol stream includes at least one of a $C_4$ to $C_{13}$ alcohol.

18. The method according to claim 17, wherein the alcohol stream comprises butanol, pentanol, hexanol, cyclohexanol, heptanol, 2-ethylhexanol, cyclohexanemethanol, isomers of methylcyclohexanemethanol, octanol, nonanol, benzyl alcohol, 2-phenyl ethanol, or decanol or mixtures thereof.

19. The method according to claim 8, wherein the furan-2,5-dicarboxylate derivative plasticizer comprises dibutyl furan-2,5-dicarboxylate, dipentyl furan-2,5-dicarboxylate, dihexyl furan-2,5-dicarboxylate, diheptyl furan-2,5-dicarboxylate, bis(2-ethylhexyl) furan-2,5-dicarboxylate, bis(dioctyl) furan-2,5-dicarboxylate, bis(dibenzyl) furan-2,5-dicarboxylate, bis(dinonyl) furan-2,5-dicarboxylate, or bis(didecyl) furan-2,5-dicarboxylate or mixtures thereof.

20. The method according to claim 10, wherein the hydrogenation catalyst comprises a nickel catalyst, a palladium catalyst, a platinum catalyst, a ruthenium catalyst, or a rhenium catalyst or mixtures thereof.

21. The method according to claim 10, wherein the esterification catalyst comprises dibutyltin diacetate, dibutyltin oxide, titanium tetraisopropoxide, zirconium derivatives, iron derivatives, sulfuric acid, methanesulfonic acid, or hydrochloric acid or mixtures thereof.

22. The method according to claim 10, wherein the esterification is conducted at a temperature below 125° C.

23. The method according to claim 22, wherein the esterification temperature is conducted at a temperature below 100° C.

24. The method according to claim 10, wherein hydrogenation is conducted at a pressure below 400 psig.

25. The method according to claim 24, wherein hydrogenation is conducted at a pressure below 200 psig.

26. The method according to claim 10, wherein the hydrogenation is conducted at a temperature below 200° C.

* * * * *